United States Patent [19]

Ghebre-Sellassie et al.

[11] Patent Number: 4,616,022

[45] Date of Patent: Oct. 7, 1986

[54] PROCATEROL STABILIZATION

[75] Inventors: Isaac Ghebre-Sellassie, Randolph; Russell U. Nesbitt, Jr., Somerville, both of N.J.

[73] Assignee: Warner-Lambert Company, Morris Plains, N.J.

[21] Appl. No.: 641,631

[22] Filed: Aug. 17, 1984

[51] Int. Cl.[4] .................... C07D 215/22; A61K 31/47
[52] U.S. Cl. ..................................... 514/312; 546/157
[58] Field of Search ..................... 424/258; 546/157; 514/312

[56] References Cited

U.S. PATENT DOCUMENTS 4,026,897  5/1977  Nakagawa ........................... 424/258

FOREIGN PATENT DOCUMENTS 1100570  1/1966  United Kingdom .
1108320  4/1968  United Kingdom .

OTHER PUBLICATIONS

Morrison and Boyd, "Organic Chemistry" 3rd Edition, p. 745.
Cadormiga Chemical Abstracts 68:6157g (1965).
Derwent Abstract C 83-079234 (1983).
Physician's Desk Reference 31st Ed., pp. 1138 and 1270 (1977).
Merck Index 9th Edition, pp. 110, 111, 300, 1116.
Merck Index 9th Edition, pp. 829 and 830 (1976).

Primary Examiner—Christine M. Nucker
Assistant Examiner—Robert Benson
Attorney, Agent, or Firm—Sandra M. Person

[57] ABSTRACT

Procaterol, and pharmaceutically active forms thereof, can be rendered resistant to attack by moisture and air via reaction with certain stabilizing reagents.

2 Claims, No Drawings

PROCATEROL STABILIZATION

BACKGROUND

Procaterol, 8-hydroxy-5[1-hydroxy-2-[(1-methylethyl)amino]butyl]-2-(1H)-quinolinone, is active as a bronchodilator, exhibiting selective beta-adrenergic agonist activity. However, its pharmaceutically-acceptable forms are readily oxidatively decomposed in the presence of moisture and air to undesirable compounds.

THE INVENTION

It has been discovered that the biologically-active form of procaterol can be stabilized to render it oxidation- and moisture-resistant by converting it to stable derivatives via interactions with certain anions preferably that derived from ammonium lauryl sulfate. The stable derivatives can then be used in conventional pharmaceutical delivery systems, e.g., in combination with a carrier in a unit dosage form.

ADVANTAGES

The instant invention has several advantages over the prior art. The stabilized procaterol derivative need not be specifically handled or packaged to prevent contact with moisture and/or air. The use of other constituents, e.g., antioxidants or scavengers, in the drug or in its containments is no longer necessary.

Furthermore, the stabilized forms of procaterol which are produced in accordance with the invention have relatively low solubility in gastrointestinal fluids, so that they can be used in prolonged action dosage forms.

Other aspects and advantages will become apparent from a consideration of the following description and claims.

DESCRIPTION OF THE INVENTION

The invention rests on the discovery that stable, oxidation- and moisture-resistant derivatives of procaterol can be produced by contacting procaterol or pharmaceutically-acceptable forms thereof with a stabilizing reagent which contains a readily ionizable anionic moiety. The mechanism of interaction between the procaterol base and the stabilizing reagent is such that, in the case of an organic sulfate, a procaterol organo sulfate is produced. This product is more stable against moisture and air than is the procaterol base. Nonetheless, it is effective as an active component of a drug formulation.

The Procaterol Base

The instant invention provides a way to stabilize procaterol and its pharmaceutically-acceptable forms, e.g., salts. Mixtures of procaterol and one or more of these forms can be used.

Procaterol has the following structural formula:

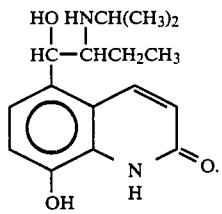

(I)

When treated with one or more suitable reagents it can be converted to other pharmaceutically-acceptable forms, e.g., salts. One such form is procaterol hydrochloride.

Procaterol is believed to decompose in the presence of moisture and air to give 5-formyl-8-hydroxycarbostyril, propionaldehyde and isopropylamine:

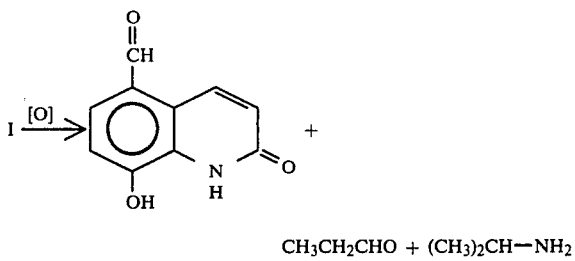

$CH_3CH_2CHO + (CH_3)_2CH—NH_2$

Stabilizing Reagents

The stabilizing reagents of the invention are substances which react with procaterol bases to yield products having greater stability in the presence of moisture and/or air than untreated procaterol bases.

Generally, the reagents employed are organic salts, that is, carboxylates, phosphates and/or sulfates conforming to the general formulas $RCOOX$, $ROPO_3X$, and $RSO_3X$, respectively, wherein R is an organic radical containing from about 5 to about 20 carbon atoms, preferably about 10 to about 15 carbon atoms, and X is a monovalent metal or ammonium moiety. Mixtures of such reagents are operable.

Preferred stabilizing reagents include ammonium dodecyl benzene sulfate, ammonium lauryl sulfate, alkali metal organo sulfates, e.g., potassium lauryl sulfate, sodium octadecyl benzene sulfate, and the like. Ammonium lauryl sulfate and sodium lauryl sulfate are highly preferred.

The molar ratio of procaterol and/or procaterol salts to stabilizing reagent will generally be on the order of about 10:1 to about 1:10 with ratios of about 1:1 preferred. Equivalent amounts of reactants are highly preferred.

Acid Reagent

The reaction of the procaterol or procaterol derivative and the stabilizing reagent takes place in an acidic environment, i.e., under acidic conditions. By "acidic conditions" applicants' refer to the state in which protons are present in the reaction medium. Since a liquid, e.g., aqueous, reaction medium is preferred, the use of substances which increase the hydrogen ion concentration—i.e., lower the pH—of liquids are operable.

Useful reagents include buffered and unbuffered organic and inorganic acids which dissolve the principal reactants. Preferred species include sulfuric acid, nitric acid, hydrochloric acid, acetic acid and citrate buffer. Hydrochloric acid is highly preferred.

The quantity of acid reagent to be employed can be readily determined by routine experimentation. Generally acids can be used at concentrations of about 0.01 to about 10 wt %, and preferably about 0.1 to about 5 wt %, based on the total weight of the initial reaction medium.

EXAMPLE

Procaterol lauryl sulfate is prepared by reacting equimolar quantities of procaterol and lauryl sulfate ion in an acidic environment as follows: dissolve separately 1 gm of procaterol and 0.97 gm of ammonium lauryl sulfate in 100 ml of 0.1N HCl. Mix the two solutions with stirring. A white precipitate is instantly produced. Continue stirring for thirty minutes to ensure maximum yield. After allowing the mixture to stand at room temperature overnight, filter, wash the precipitate thoroughly with distilled water, and dry at 45°.

The stabilization reaction can be characterized as follows:

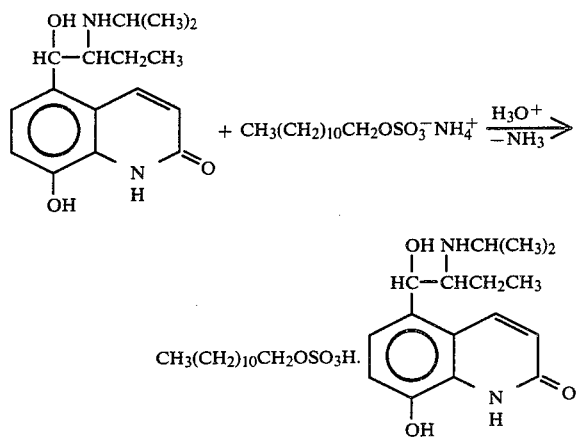

Procaterol lauryl sulfate and other stabilized forms of procaterol made in accordance with the invention are much less susceptible to oxidative degradation than procaterol or its hydrochloride salt in the presence of moisture and air. Procaterol lauryl sulfate is an odorless, white powder that is sparingly soluble in water and gastrointestinal fluids but freely soluble in methanol and ethanol.

The extra stability imparted to procaterol via conversion to, e.g., procaterol lauryl sulfate, can alleviate the instability problem commonly associated with procaterol formulations. The insolubility of the compound in gastrointestinal fluids coupled with the microgram dose of procaterol makes the salt a good candidate for the development of prolonged action dosage forms of the drug.

Reasonable variations, such as those which would occur to a skilled artisan, can be made herein without departing from the scope of the invention.

We claim:

1. An oxidation- and moisture-resistant salt of procaterol produced by contacting, in an acidic environment, at least one reactant selected from the group consisting of procaterol and pharmaceutically acceptable salts of procaterol with at least one reagent selected from the group consisting of the monovalent metal and ammonium salts of lauryl sulfate.

2. A bronchodilating drug in unit dosage form consisting essentially of the salt of claim 1 and a suitable carrier.

* * * * *